US 10,457,747 B2
Oct. 29, 2019

(12) United States Patent
Chea et al.

(10) Patent No.: US 10,457,747 B2
(45) Date of Patent: Oct. 29, 2019

(54) METHOD FOR OBTAINING HIGH-YIELD, STABLE EXPRESSION CELL CLONES AND ANTIBODY MOLECULES OBTAINED THEREBY

(71) Applicants: BIOTECH PHARMACEUTICAL CO. LTD, Beijing (CN); CENTRO DE INMUNOLOGIA MOLECULAR, Havana (CU)

(72) Inventors: MeyLen Chea, Havana (CU); Julio Palacios, Havana (CU); Miguel Arias, Havana (CU); Loany Calvo, Havana (CU); Tamara González, Havana (CU); Rolando Pérez, Havana (CU); Zhi Bai, Shanxi Province (CN); Yuemao Liu, Hunan Province (CN); Kaiheng Xiao, Beijing (CN); Xiao Chen, Henan Province (CN); Zhenhua He, Beijing (CN); Yangliu Cai, Beijing (CN); Zhenhua Yang, Shan Xi Sheng (CN); Xianhong Bai, Beijing (CN)

(73) Assignees: BIOTECH PHARMACEUTICAL CO. LTD., Beijing (CN); CENTRO DE INMUNOLOGIA MOLECULAR, Havana (CU)

( * ) Notice: Subject to any disclaimer, the term of this patent is extended or adjusted under 35 U.S.C. 154(b) by 123 days.

(21) Appl. No.: 15/549,087

(22) PCT Filed: Mar. 11, 2016

(86) PCT No.: PCT/CN2016/076135
§ 371 (c)(1),
(2) Date: Aug. 4, 2017

(87) PCT Pub. No.: WO2016/127954
PCT Pub. Date: Aug. 18, 2016

(65) Prior Publication Data
US 2018/0016353 A1    Jan. 18, 2018

(30) Foreign Application Priority Data
Feb. 14, 2015   (CN) .......................... 2015 1 0080631

(51) Int. Cl.
C07K 16/44      (2006.01)
C12P 21/02      (2006.01)
A61K 39/00      (2006.01)

(52) U.S. Cl.
CPC .............. *C07K 16/44* (2013.01); *C12P 21/02* (2013.01); *A61K 2039/505* (2013.01); *C07K 2317/14* (2013.01); *C07K 2317/24* (2013.01); *C07K 2317/73* (2013.01); *C07K 2317/92* (2013.01)

(58) Field of Classification Search
CPC ........................ C07K 2317/14; C12N 5/0694
See application file for complete search history.

(56) References Cited

U.S. PATENT DOCUMENTS 6,429,295 B1    8/2002  Carr Perez et al.

FOREIGN PATENT DOCUMENTS

CN    1809592 A       7/2006
CN    104152415 A     11/2014
CN    104651314 A     5/2015

OTHER PUBLICATIONS

Woodside et al (Cytotechnology, 1998, vol. 28, pp. 163-175) (Year: 1998).*
Castillo et al (Animal Cell Technology meets Genomics, 2005, pp. 505-508, Springer, F Godia and M. Fussenegger, Ed.s) (Year: 2005).*
Freshney (The Culture of Animal Cells, Third Edition, 1994, pp. 254-255) (Year: 1994).*
Prieto et al (Cytotechnology, 2011, vol. 63, pp. 351-362) (Year: 2011).*
Barnes et al., "Advances in animal cell recombinant protein production: GS-NS0 expression system," Cytotechnology 32: pp. 109-123, 2000.
Barnes et al., "Stability of Protein Production From Recombinant Mammalian Cells," Biotechnology and Bioengineering, vol. 81, No. 6, Mar. 20, 2003, pp. 631-639.
Barnes et al., "Molecular Definition of Predictive Indicators of Stable Protein Expression in Recombinant NS0 Myeloma Cells," Biotechnology and Bioengineering, vol. 85, No. 2, Jan. 20, 2004, pp. 115-121.
Barnes et al., "Molecular Analysis of Successful Cell Line Selection in Transfected GS-NS0 Myeloma Cells," Biotechnology and Bioengineering, vol. 96, No. 2, Feb. 1, 2007, pp. 337-348.
Blanco et al., "Tissue Reactivity of the 14F7 Mab Raised against N-Glycolyl GM3 Ganglioside in Tumors of Neuroectodermal, Mesodermal, and Epithelial Origin," Journal of Biomarkers, vol. 2013, Article ID 602417, pp. 1-9.
"Demonstration of Comparability of Human Biological Products, Including Therapeutic Biotechnology-derived Products," Center for Biologics Evaluation and Research (CBER), Center for Drug Evaluation and Research (CDER), Apr. 1996, pp. 1-8.
Carr et al., "A Mouse IgG1 Monoclonal Antibody Specific for N-Glycolyl GM3 Ganglioside Recognized Breast and Melanoma Tumors," Hybridoma, vol. 19, No. 3, 2000, pp. 241-247.

(Continued)

*Primary Examiner* — Karen A. Canella
(74) *Attorney, Agent, or Firm* — Hoffmann and Baron, LLP

(57) ABSTRACT

Provided is a method for obtaining high-yield, stable expression cell clones from myeloma cell lines in a protein-free culture medium. The method is used for industrial production of a recombinant antibody, and includes three stage: (1) adapting to a protein-free culture medium, statically culturing cells at a low density, and gradually reducing a fat-rich supplement to a chemical culture medium; (2) adapting to a protein-free culture medium; culturing cells at a high density, and using a perfusion fermentation system in a laboratory scale; and (3) screening high-yield, stable expression cell clones from the cells after fermentation ends. The cell clone may be used to produce a humanized anti-NeuGcGM3 14F7 recombinant antibody.

5 Claims, 16 Drawing Sheets

(56) References Cited

OTHER PUBLICATIONS

Carr et al., "In Vivo and In Vitro Anti-Tumor Effect of 14F7 Monoclonal Antibody," Hybridoma, vol. 21, No. 6, 2002, pp. 463-468.
Biologics Medicines in Development, 2013 Report, Presented by America's Biopharmaceutical Research Companies, pp. 1-87.
Blanco et al., "Immunorecognition of the 14F7 Mab Raised against N-Glycolyl GM3 Ganglioside in Some Normal and Malignant Tissues from Genitourinary System," International Scholarly Research Network, ISRN Pathology, vol. 2011, Article ID 953803, pp. 1-10.
Blanco et al., "Immunoreactivity of the 14F7 Mab Raised against N-Glycolyl GM3 Ganglioside in Epithelial Malignant Tumors from Digestive System," International scholarly Research Network, ISRN Gastroenterology, vol. 2011, Article ID 645641, pp. 1-9.
Fernandez-Marrero et al., "A cytotoxic humanized anti-ganglioside antibody produced in a murine cell line defective of N-glycolylated-glycoconjugates," Immunobiology 216 (2011) pp. 1239-1247.
Hartman et al., "Derivation and Characterization of Cholesterol-Independent Non-GS NS0 Cell Lines for Production of Recombinant Antibodies," Biotechnology and Bioengineering, vol. 96, No. 2, Feb. 1, 2007, pp. 294-306.
Hayashi et al.,"Detection of N-glycolyated gangliosides in non-small-cell lung cancer using GMR8 monoclonal antibody," Cancer Science, Jan. 2013, vol. 104, No. 1, pp. 43-47.
Keen et al., "Adaptation of cholesterol-requiring NS0 mouse myeloma cells to high density growth in a fully defined protein-free and cholesterol-free culture medium," Cytotechnology, vol. 17, 1995, pp. 203-211.
Marquina et al., "Gangliosides Expressed in Human Breast Cancer," Cancer Research, vol. 56, Nov. 15, 1996, pp. 5165-5171.
Mateo et al., "Removal of Amphipathic Epitopes from Genetically Engineered Antibodies: Production of Modified Immunoglobulins with Reduced Immunogenicity," Hybridoma, vol. 19, No. 6, 2000, pp. 463-471.
Montesino et al., "Structural characterization of N-linked oligosaccharides on monoclonal antibody Nimotuzumab through process development," Biologicals, vol. 40, 2012, pp. 288-298.
Oliva et al., "Clinical evidences of GM3 (NeuGe) ganglioside expression in human breast cancer using the 14F7 monoclonal antibody labelled with 99mTc," Breast Cancer Research and Treatment, vol. 96, 2006, pp. 115-121.
Osorio et al., "Heterophilic NeuGcGM3 ganglioside cancer vaccine in advanced melanoma patients: Results of a phase Ib/IIa study," Cancer Biology & Therapy, 7:4, pp. 488-495. 2008.
Pluschke et al., "Determination of intracellular antibody production, cell density, and viability of recombinant CHO-DG44 cells using the MACSQuant Analyzer," Meeting Abstract—BMC Proceedings, 2011, Suppl. 8, pp. 1-3.
ICH Harmonised Tripartite Guideline, Comparability of Biotechnological/Biological Products Subject to Changes in Their Manufacturing Process, Q5E, International Conference on Harmonisation of Technical Requirements for Registration of Pharmaceuticals for Human Use, dated Nov. 18, 2004, Published in the Federal Register, vol. 70, No. 125, Jun. 30, 2005, www.ich.org/fileadmin/Public_Web_Site/ICH_Products/Guidelines/Quality/Q5E/Step4/Q5EGuideline.pdf, pp. 1-12.
Roque-Navarro et al., "Anti-ganglioside antibody-induced tumor cell death by loss of membrane integrity," Mol cancer Ther 2008;7(7), Jul. 2008, pp. 2033-2041.
Scursoni et al., "Detection and Characterization of N-Glycolyated Gangliosides in Wilms Tumor by Immunohistochemistry," Pediatric and Developmental pathology 13, 2010, pp. 18-23.
Scursoni et al., "Detection of N-Glycolyl GM3 Ganglioside in Neuroectodermal Tumors by Immunohistochemistry: An Attractive Vaccine Target for Aggressive Pediatric Cancer," Clinical and Developmental immunology, vol. 2011, Article ID 245181, pp. 1-6.
Walsh, Gary, "Biopharmaceutical benchmarks 2014," Nature Biotechnology, vol. 32, No. 10, Oct. 2014, pp. 992-1000.
Zhang et al., "Development of animal-free, protein-free and chemically-defined media for NS0 cell culture," Cytotechnology, 2005, 48: pp. 59-74.
Van Cruijsen et al., "Tissue micro array analysis of ganglioside N-glycolyl GM3 expression and signal transducer and activator of transcription (STAT)-3 activation in relation to dendritic cell infiltration and microvessel density in non-small cell lung cancer," BMC Cancer, 9:180, pp. 1-9, 2009.
Committee for Priprietary Medicinal Products (CPMP), The European Agency for the Evaluation of Medicinal Products, "Guideline on Comparability of Medicinal Products Containing Biotechnology-Derived Proteins as Active Substance-Non-Clinical and Clinical Issues," London, Dec. 17, 2003, www.emea.europa.eu/pdfs/human/bwp/320700en.pdf, pp. 1-11.
Freshney, R., "Culture of animal cells: a manual of basic technique and specialized applications," 2010, (6th ed.), Hoboken, N.J., Wiley-Blackwell, pp. 208-211.

* cited by examiner

METHOD FOR OBTAINING HIGH-YIELD, STABLE EXPRESSION CELL CLONES AND ANTIBODY MOLECULES OBTAINED THEREBY

CROSS-REFERENCE TO RELATED APPLICATIONS

This application is the U.S. National Phase of, and Applicants claim priority from, International Patent Application Number PCT/CN2016/076135 filed Mar. 11, 2016, which claims priority from CN201510080631.3 filed Feb. 14, 2015, each of which is incorporated herein by reference.

FIELD OF INVENTION

The present invention relates to biotechnology, specifically to an efficient method to select stable high producer cell clones to be used in perfusion fermentation processes in order to produce therapeutic antibodies.

BACKGROUND OF THE INVENTION

Therapeutic antibodies constitute the major category of biopharmaceuticals into the marketplace (Walsh G, 2014, Nature Biotechnology 2014, 32: 992-1000). Several therapeutic antibodies have obtained registration approval for the treatment of cancer, autoimmune diseases and other chronic diseases and dozens of recombinant antibodies are in different phases of clinical development (Biologic Medicines in Development, Phrma Report 2013, www.phrma.org). Usually patients receive hundreds milligrams of therapeutic antibodies in each dose, therefore there is currently a huge demand of production capacity worldwide.

Several approaches have been followed to increase the productivity of the industrial cell lines, for example, gene amplification systems, cell culture medium optimization and methods to select high producer cell clones. Genetic modification and epigenetic adaptation of recombinant myeloma cell lines to produce therapeutic antibodies is currently a very competitive research field (Barnes et al., 2000, Cytotechnology 32:109-123; Barnes et al., 2007, Biotechnol Bioeng 96:337-349).

Perfusion fermentation-based production processes allow high density cell cultures and potentially high antibody concentration in fermentation harvest. However long-term high density cell culture requires stable high producer clones to really optimize antibody production. Protein-free media have been developed for biopharmaceutical production, for example PFHMII cell culture medium (reference from Hyclone).

Recombinant antibody-producing NS0 cell clones have been successfully adapted to grow in protein-free media (WO 2004/038010 A1). However, adaptation to serum free-media and further long-term fermentation process in serum-free media are most usually accompanied by a loss of cell line productivity (Barnes et al., 2003, Biotechnol Bioeng 81: 631-639; Barnes et al., 2004, Biotechnol Bioeng 85: 115-121). Stable high producer cell clones adapted to grow in protein-free medium can be recovered from unstable recombinant myeloma cell lines for industrial use (CN104152415A).

But in practice for some recombinant myeloma cell lines the process of adaptation from serum-free medium to protein-free medium is not possible or takes long-time and is accompanied by the loss of antibody production due to the emergence of non-producer cell population. Innovation in the selection process of cell clones with industrial potential is warranted.

Biopharmaceuticals, in particular therapeutic antibodies, are complex glycoprotein molecules. Any change in the production process might introduce variations in product attributes. The concept of comparability has emerged to assess such variations in product attributes (Demonstration of comparability of human biological products, including therapeutic biotechnology-derived products, Center for Biologics Evaluation and Research (CBER), Center for Drug Evaluation and Research (CDER) April 1996. www.fda.gov/Drugs/GuidanceComplianceRegulatoryInformation/Guidances/ucm122879.htm; EU Guideline on Comparability of Medicinal Products containing Biotechnology-derived Proteins as Active Substances: Quality issues (CPMP December 2003). www.emea.europa.eu/pdfs/human/bwp/320700en-.pdf; ICH Q5E: Comparability of Biotechnological/Biological Products Subject to Changes in their Manufacturing Process. EU: Adopted by CMPM, Dec. 1, 2004, CPMP/ICH/5721/03, date for coming into operation: June 2005; MHLW: Adopted 26 Apr. 2005, PFSB/ELD Notification No. 0426001; FDA: Published in the Federal Register, Vol. 70, No. 125, Jun. 30, 2005; 37861-2 www.ich.org/fileadmin/Public_Web_Site/ICH_Products/Guidelines/Quality/Q5E/Step4/Q5E_Guideline.pdf). Change in the cell line is considered one the critical modification in the production process. Therefore although selection of cell lines with industrial potential is absolutely required in the production process development it is not obvious that any of the selected cell lines with the required characteristics of stability and high production rate will be suitable because variations in the secreted immunoglobulin might affect its biological properties. Definition of identity attributes of each specific antibody is a prerequisite for any further comparability studies related to production process modification, for example production scale or manufacturing site.

14F7 is a monoclonal antibody (mAb) specific for the tumor associated antigen N-glycolyl-GM3 ganglioside [GM3(Neu5Gc)] (Patent number ZL 99800261.5; Carr et al., 2000, Hybridoma 19, 241-247). This antigen has been detected in breast cancer (Marquina et al., 1996, Cancer Res 56, 5165-5171; Oliva et al., 2006, Breast Cancer Res Treat 96, 115-121), melanoma (Osorio et al., 2008, Cancer BiolTher 7, 488-495), non-small cell lung cancer (van Cruijsen et al., 2009, BMC Cancer 9, 180; Hayashi et al., 2013, Cancer Sci 104, 43-47), Wilms tumors (Scursoni et al., 2010, Pediatr Dev Pathol 13, 18-23), neuroectodermal tumors (Scursoni et al., 2011, Clin Dev Immunol 245181), sarcomas and thyroid carcinomas (Blanco et al., 2013, Journal of Biomarkers, 602417) and malignancies from the digestive (Blanco et al., 2011, ISRN Gastroenterol 645641) and genitourinary (Blanco et al., 2011, ISRN Pathology, 953803) systems.

14F7 mAb is able to kill tumor cells expressing the ganglioside in a complement-independent manner (Carr et al., 2002, Hybrid Hybridomics 21, 463-468; Roque-Navarro et al., 2008, Mol Cancer Ther 7, 2033-2041). A humanized version of this antibody, obtained by the modification of potential human T cell epitopes (Patent application No. 200480017457.8; Mateo et al., 2000, Hybridoma 19, 463-471) and named 14F7h, retained the properties of the mouse and chimeric antibodies (Fernandez-Marrero et al., 2011, Immunobiology 216, 1239-1247). Humanized 14F7hmAb is of potential value for the therapy of GM3(NeuGc)-expressing tumors. [0010] However recombinant NS0 myeloma cell lines expressing antibody 14F7h lost viability in high density cell cultures because these cells expressed the antigen GM3(Neu5Gc) and were killed by the secreted cytotoxic antibody. Therefore the recombinant humanized antibody 14F7h was expressed in murine NS0 myeloma cell line defective in N-glycolylated-glycoconjugates, due to the knock down of the CMP-N-acetylneuraminic acid hydroxylase enzyme (Fernandez-Marrero et al., 2011, Immunobiology 216, 1239-1247). Such cell line showed to be very difficult to adapt to grow in serum-free medium.

In the present invention we have established a new approach to develop stable high producer cell clones to be used in perfusion fermentation production process. Following this approach cell clones were recovered from a recombinant NS0 myeloma cell line which produces an anti-GM3 (NeuGc) monoclonal antibody. Identity attributes of such therapeutic antibody are also disclosed in this invention, which define a molecular phenotype for this biopharmaceutical.

DETAILED DESCRIPTION OF THE INVENTION

This procedure comprises recombinant myeloma cell lines for which the process of adaptation from serum-free medium to protein-free medium is not possible or takes long-time and is accompanied by the loss of antibody production due to the emergence of non-producer cell population. Key innovative step in the present invention is the adaptation process to grow in protein-free medium in high cell density ($8-10 \times 10^6$ cells/ml) which increases the frequency of stable high producer cell clones.

The method of the present invention consists of three stages process:
1. Adaptation to protein-free medium by a stepwise reduction of a lipid-enriched supplement to chemically defined medium in low density stationary cell culture
2. Adaptation to protein-free medium in high density cell culture using perfusion fermentation system at lab scale
3. Selection of stable high producer cell clones from cells at the end of fermentation The first stage was performed by defrosting the cell line in protein-free cell culture medium (PFHMII) supplemented with 3-4 g/L of Cell Boost (enriched in cholesterol, lipids and other nutrients). Maximal cell concentration (Xv) was ranging from $0.9-1.2 \times 10^6$ cell/ml. Serial passage was performed until Xv reached a constant value. Initial cellular concentration after each passage was adjusted to $0.4-0.5 \times 10^6$ cell/ml. After seven passages Cell Boost supplement was reduced to 1-2 g/L, and after four additional passages Cell Boost supplement was completely removed. Then cells were allowed to grow in protein-free medium without any supplement for more than 60 days. Xv reached values between $1.5-1.8 \times 10^6$ cell/ml with around 95% cell viability.

As second stage, cells growing for more than 60 days in PFHMII cell culture medium were seeded in a 5 liters bioreactor. Using a perfusion external device the cell concentration grew from $0.5 \times 10^6$ to $10 \times 10^6$ cells/ml. The fermentation process lasted for 24 days. From day 0 to 16 the cell viability was maintained above 90% but after day 16 cell viability was reduced below 80%. Average antibody concentration in the cell harvest was 30-40 mg/ml. Cells at the end of fermentation (more than 500 hours growing in protein-free medium) were frozen and storage in liquid nitrogen (End Production Cell Bank, EPCB).

In another embodiment of the present invention stable high producer cell clones from cells at the end of fermentation were selected. Defrosted cells from EPCB were subjected to cell cloning by the limiting dilution method (Freshney R., 2010, Culture of animal cells: a manual of basic technique and specialized applications (6th ed.). Hoboken, N.J.: Wiley-Blackwell. pp. 208-211). Secreted antibody in cell culture supernatant was measured by an ELISA method using the anti-14F7h MAb anti-idiotypic antibody 4G9 as capture antigen. Cell culture supernatants were diluted 1/500. Clones yielding absorbance values above the median one were selected for further characterization by Flow Cytometry (FACS), Intracellular immunoglobulin staining was performed using an anti-human IgG antibody conjugated with FITC and measured by FACS (Pluschke et al., 2011, BMC Proceedings 5, Suppl 8:P97). Mean Fluorescence Intensity (MFI) and percentage of positive cells were determined for each isolated clone. Surprisingly more than 80% of evaluated clones showed a predominant antibody-producer subpopulation.

Clones having more than 95% antibody-producer subpopulation and higher MFI were selected for kinetic studies in spinner flasks and 5 L bioreactor to evaluate cell concentration (Xv), cell viability (%), specific growth rate (p) and IgG concentration in cell culture supernatant. Cell concentration was found between $4-5 \times 10^6$ cells/ml. Cell viability during the exponential growth phase was about 85%. Specific growth rate varied between $0.015-0.025$ $h^{-1}$. IgG concentration was found between 70-120 mg/L.

In another embodiment of the present invention, long-term stability of stable high producer cell clones was evaluated by performing kinetic studies after 30, 60 and 90 days in continuous cell culture. Specific growth rate (p) and specific production rate (qp) were determined.

In still another embodiment of the present invention, identity attributes of the secreted immunoglobulin by selected stable high producer cell clones were determined. Disclosure of such identity attributes operationally defines the molecular phenotype of this therapeutic antibody 14F7h:

| Identity attributes | Molecular features | Analytical methods |
| --- | --- | --- |
| Primary structure | Molecular Mass | MS |
|  | Peptide mapping | RP-HPLC |
| High order structure | Secondary structure | Far UV CD |
|  | Tertiary structure | Intrinsic Fluorescence |
| Glycosylation | Profiling | NP-HPLC |
| Heterogeneity | Charges | WCX |
|  | Aggregation | SEC-HPLC |
| Function | Antigen recognition | Flow cytometry |

In still another embodiment of the present invention in vitro and in vivo anti-tumor activity of the recombinant antibody 14F7h were evaluated

EXAMPLES

The following Examples are intended to illustrate the invention but not to limit its scope in any way. Detailed descriptions of state of the art methods are not provided.

Example 1: Adaptation to Protein-Free Medium by a Stepwise Reduction of a Lipid-Enriched Supplement to Chemically Defined Medium in Low Density Stationary Cell Culture The cell line 14F7htb58 was adapted to growth in PFH-MII cell culture medium without supplement cell boost 5. The process of reduction of supplement cell boost 5 was performed in 75 cm$^2$ T flasks, in stirred shaker (80 rpm) at 36.5° C. and 5% $CO_2$. Every 48-72 hours the concentration of viable cells and the percentage of cell viability were determined. Cell concentration was adjusted to $0.4$-$0.5 \times 10^6$ cell/ml in every culture passage.

Figure 1:
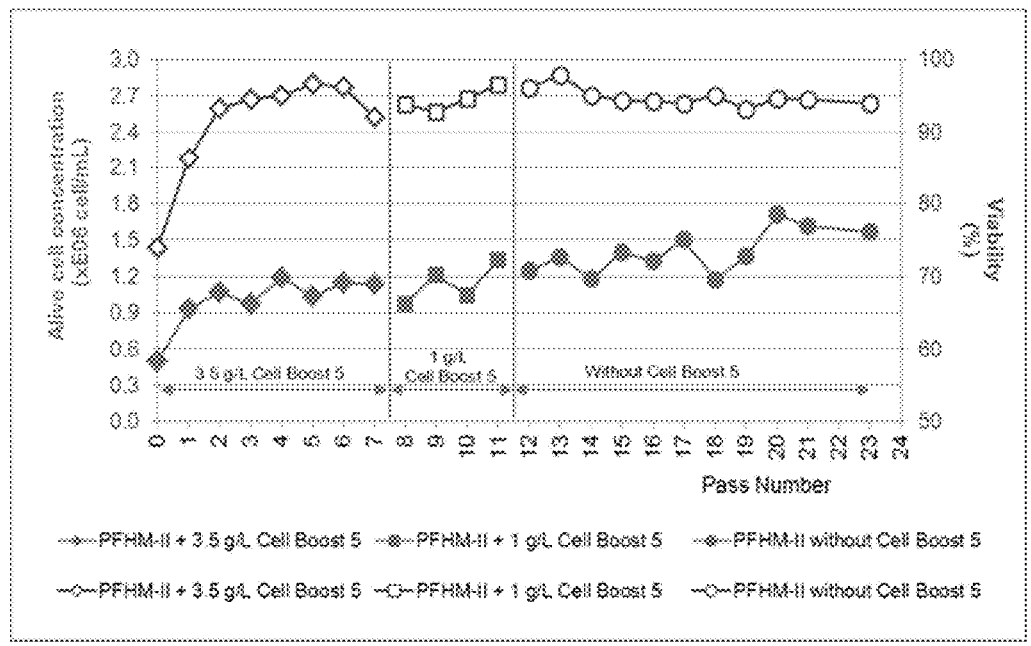
FIG. 1: Cell adaptation to PFHM-II medium at different concentrations of Cell Boost 5.

Frozen 14F7htb58 cells were thawed in PFHMII supplemented with 3.5 g/L cell boost 5. After thawing cell viability was 75%, and then it increased up to over 90% (FIG. 1). During the adaptation process, serial culture passages were performed to maintain a maximal concentration of viable cells in the range of $0.9$-$1.8 \times 10^6$ cell/ml, with percentages of cell viability higher than 90%. After eleven culture passages the concentration of cell boost 5 was reduced to zero, with 95% of cell viability and 1.2-1.8×10$^6$ cell/ml. The adaptation process to PFHMII cell culture medium without lipids and cholesterol took 60 days approximately.

Example 2: Adaptation to Protein-Free Medium in High Density Cell Culture Using Perfusion Fermentation System at Lab Scale 14F7htb58 cells adapted to growth in protein-free PFH-MII cell culture medium were inoculated in a 5 L fermenter at a concentration of 0.4-0.5×10$^6$ cell/ml. Fermenter operation parameters were: pH 6.9-7.0; 105 RPM; 40% dissolved oxygen; 36.5-37.0° C.; work volume 3.5 L. Cell viability and cell concentration were monitored daily by Trypan Blue exclusion method (Sigma) using a Neubauer chamber. Fermenter operation in perfusion mode was performed after cell concentration reached the value of 2.5×10$^6$ cell/ml. A hollow fiber cartridge was employed for the perfusion mode and a dilution rate of 0.3-0.7 VVD was used.

Figure 2:
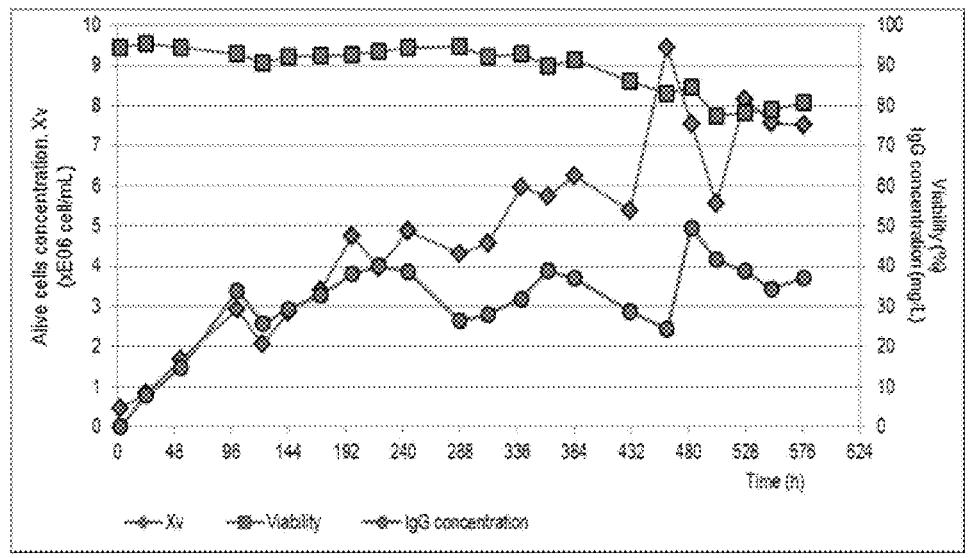
FIG. 2: Fermentation run in 5 L bioreactor using the cells adapted to PFHM-II medium without cell boost 5.

During the fermentation process cell viability kept over 90% up to 384 hours, and then it was reduced to 80%. Antibody concentration was in the range of 30-40 mg/L. The maximal cell concentration reached was 9×10$^6$ cell/ml when a dilution rate of 0.7 VVD was used (FIG. 2). Cells were taken at the end of the fermentation process and seeded in roller bottles at a concentration of 0.8×10$^6$ cell/ml, after 72 hours in culture, cells were frozen at 12×10$^6$ cell/vial (End Production Cell Bank, EPC). After thawing cell viability was 90% and after 96 hours in culture cell viability was 97%.

Figure 3:
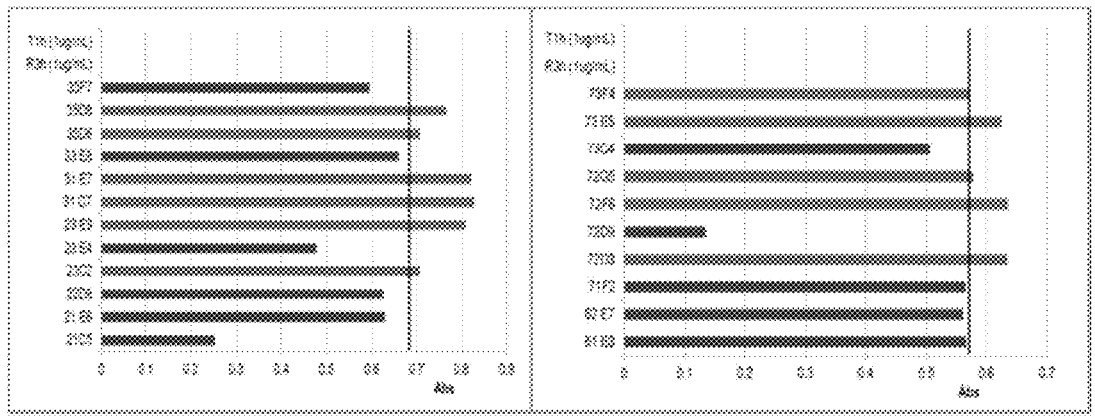
FIG. 3: Absorbance values from the recognition ELISA. Black line is the median of the results. Purified 1 μg/mL of T1h and hR3 were used as negative controls. Selected clones 35D8, 35D6, 31E7, 31C7, 23E9, 23C2, 73F4, 73E5, 72G5, 72F6, 72D3 (gray color), discarded clones 35F7, 33E8, 23E4, 22D8, 21E6, 2105, 73C4, 72D9, 71F2, 62E7, 61E3 (black color).

Example 3: Selection of Stable High Producer Cell Clones from Cells at the End of Fermentation Thawed cells from EPC were cloned to a single cell per well in 96 well plates using the limiting dilution method and DMEM-F12 1:1 cell culture medium supplemented with 5-10% of fetal bovine serum. Culture plates were incubated at 36.5° C. in 5% CO$_2$ atmosphere. Cloning efficiency was below 2%. Twenty days after cell cloning culture supernatants were taken to assess IgG concentration by sandwich-type ELISA. The anti-idiotypic antibody 4G9 (3 ug/ml) was used as capture antigen and an anti-human heavy chain goat antibody coupled to alkaline phosphatase as a probe. All samples were diluted 1/500, and the median of supernatant absorbance was determined. Clones with absorbance values higher than the median value were selected (23C2, 23E9, 31C7, 31E7, 35D6, 35D8, 72D3, 72F6, 72G5, 73E5, 73F4) (FIG. 3). Selected clones were expanded to 24 well plates in DMEM-F12 1:1 cell culture medium supplemented with 5-10% of fetal bovine serum. Further cell expansion in T culture flasks were performed using PFHMII cell culture medium, in stirred shaker (80 rpm) at 36.5° C. and 5% CO$_2$.

Figure 4:
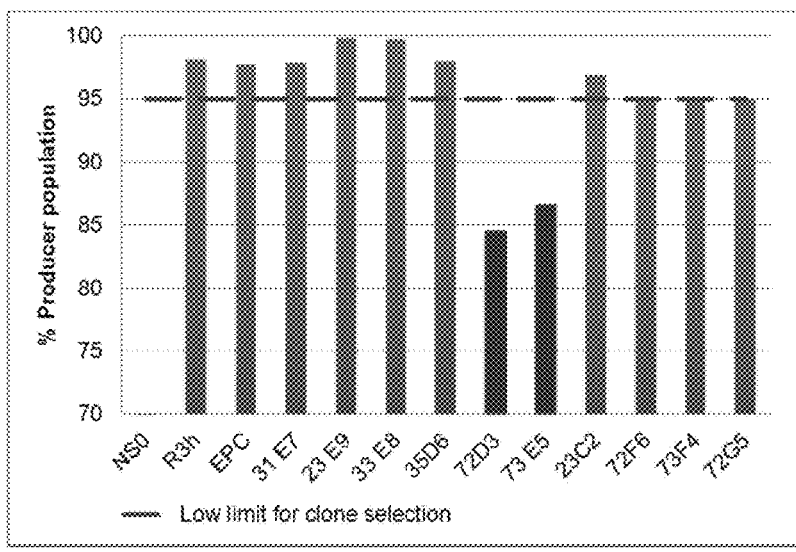
FIG. 4: Selected cells were analyzed by flow cytometry and the percentage of high producer cell sub-population was determined. NS0 myeloma cell line was used as negative control and recombinant NS0 myeloma cell line expressing hR3 antibody was used as positive control. Selected clones 31E7, 23E9, 33E8, 35D6, 23C2, 72F6, 73F4, 72G5 (gray color), discarded clones 72D3, 73E5 (black color).
Figure 5:
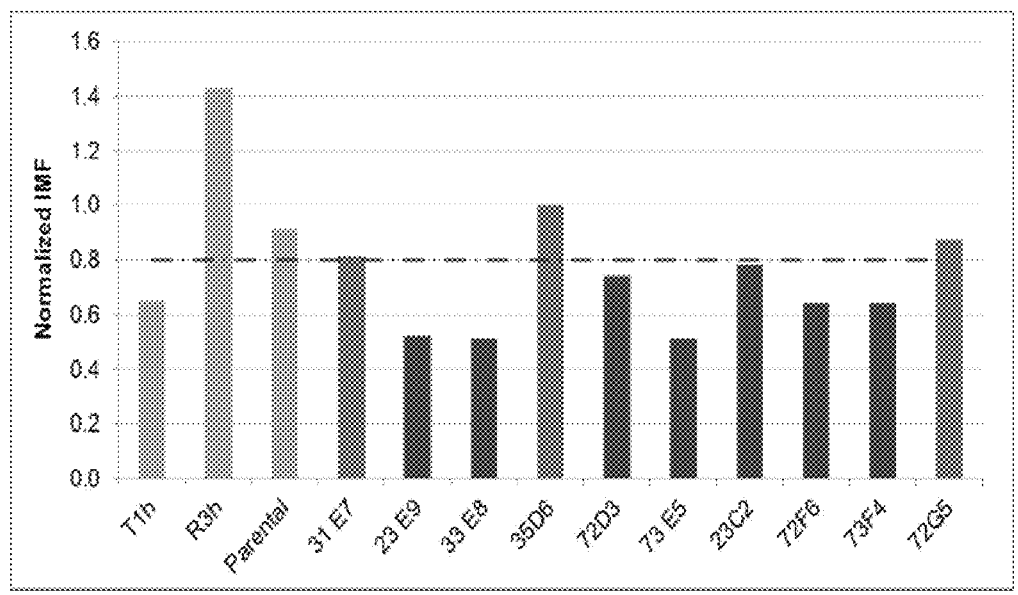
FIG. 5: MFI value of high producer cell sub-population was determined. The myeloma cell line expressing hR3 and T1h antibodies were used as positive controls (light gray color). Selected clones 31E7, 35D6, 72G5 (gray color); discarded clones 23E9, 33E8, 72D3, 73E5, 23C2, 72F6, 73F4 (black color).

Intracellular IgG content was determined by flow cytometry (FACS) in selected clones. An anti-human IgG antibody coupled to FITC (fluorescein iso-thiocyanate) (Sigma) diluted 1:200 was used as probe. To determine labeling percentage 4×10$^5$ cell/sample were analyzed. Clones having more than 95% of high producer cell sub-population were selected (FIG. 4). Another selection criterion was the normalized Fluorescence Median Intensity (FMI) and clones 35D6, 72G5 and 31E7 were selected (FIG. 5).

Figure 6:
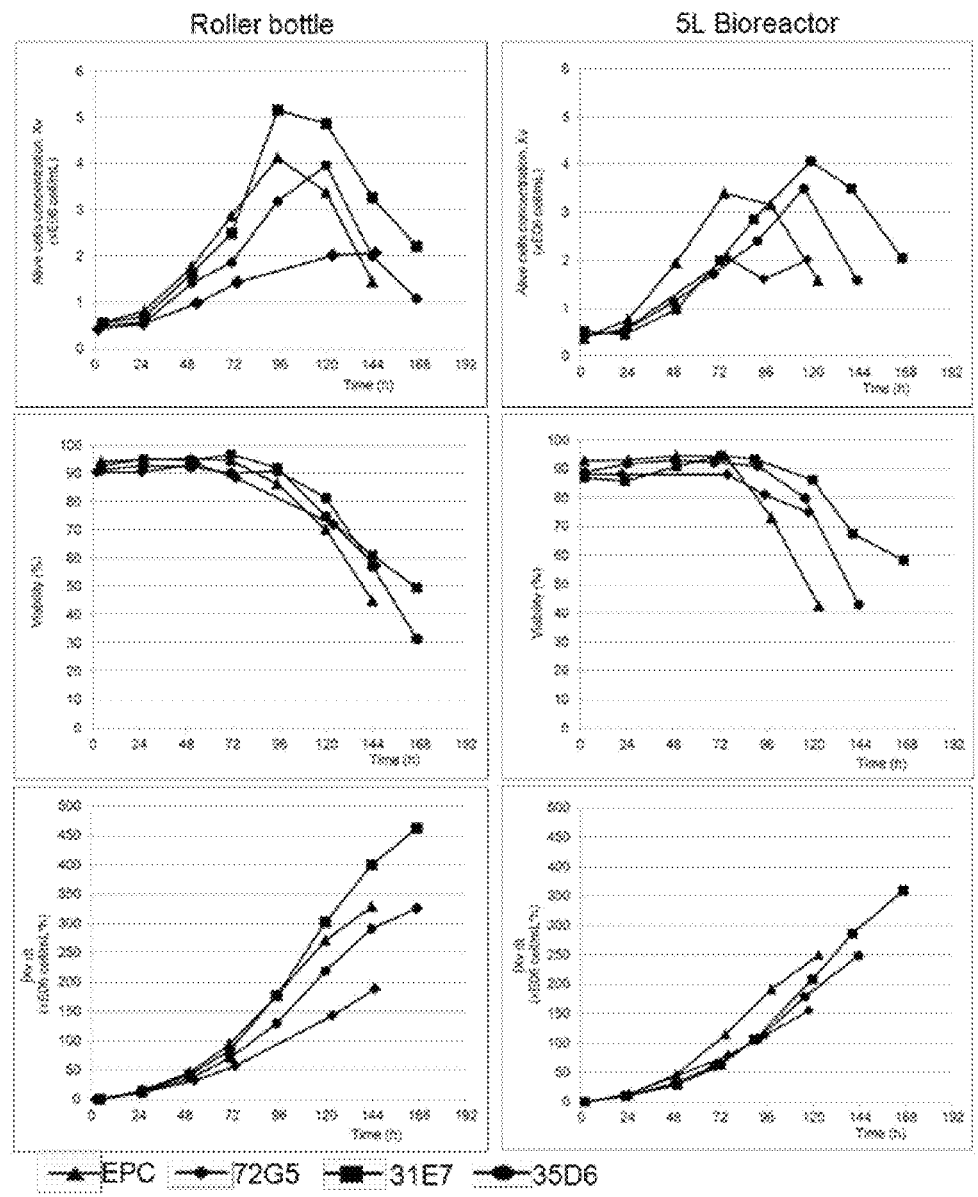
FIG. 6: Growth curves of the evaluated clones, cell viability and integral of viable cells from kinetic studies in roller bottles and 5 L bioreactor are plotted (y axis) versus time (x axis).
Figure 7:
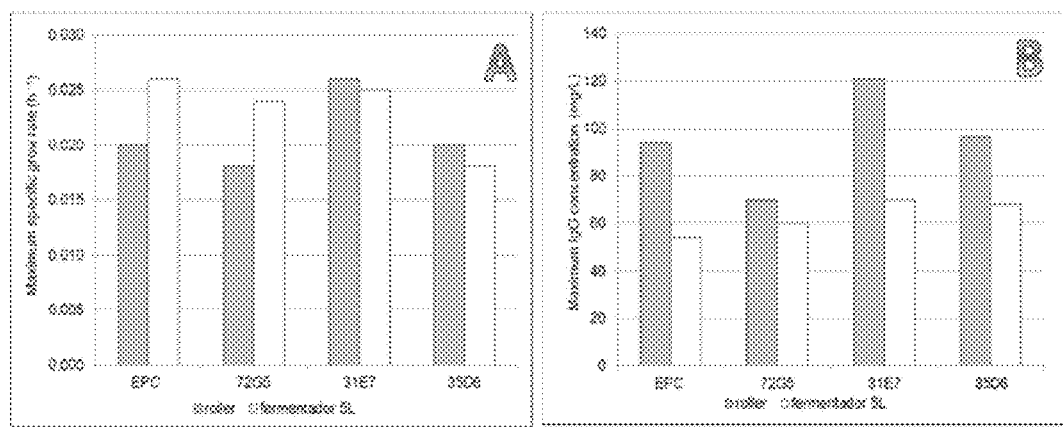
FIG. 7: Comparative analysis of maximum specific growth rate and maximum IgG concentrations between selected clones growing in roller bottles and 5 L fermenter.

Such clones were expanded in roller bottles and kinetic studies were performed also in 5 L bioreactor (36.5-37° C., 100-105 RPM, pH<7 and dissolved oxygen higher than 40%). Clone 31E7 showed the highest cell concentration in roller bottles and 5 L bioreactor, with values of 5×10$^6$ cell/ml and 4×10$^6$ cell/ml respectively. Integral of viable cells provided similar results, values of 4.5×10$^8$ cell/ml*h in roller bottles and 2.5×10$^8$ cell/ml*h in 5 L bioreactor, these values were 1.3-1.4 higher than the one obtained for parental cells (FIG. 6). Cell viability was higher than 85% in the growth exponential phase for all evaluated clones (FIG. 6). Clone 31E7 showed the highest growth specific rate (>0.025 h$^{-1}$) both in roller bottles and 5 L bioreactor. Antibody concentration between 50-70 mg/L was found for all clones in 5 L bioreactor however clone 31E7 showed the highest antibody concentration in roller bottles (FIGS. 7A and 7B).

Figure 8:
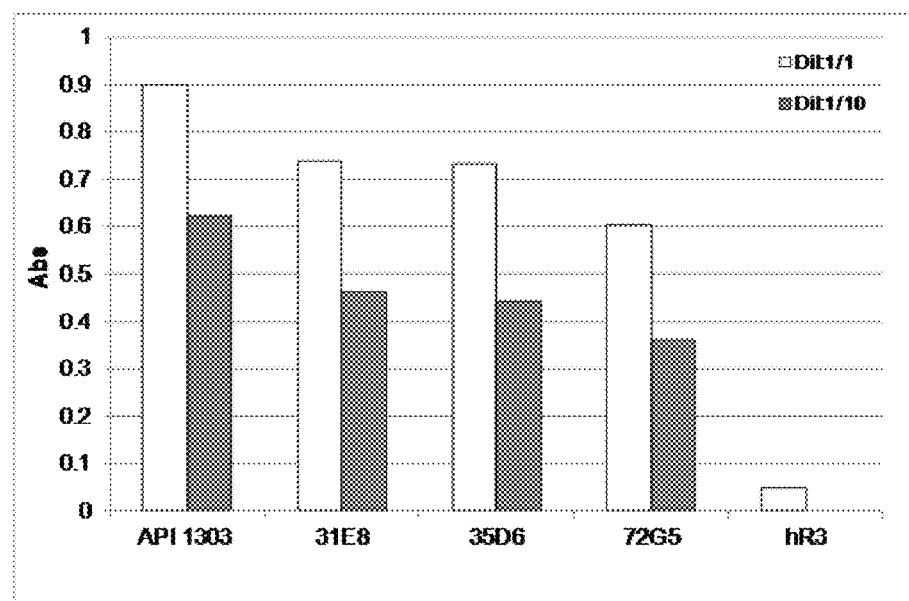
FIG. 8: Recognition of NeuGcGM3 ganglioside by 14F7h antibody produced by different selected clones. Supernatants were taken from 5 L bioreactor. The anti-EGFR antibody was used as negative control, 14F7h antibody produced by parental cell was used as positive control.

Samples were taken from the kinetic studies performed in 5 L bioreactor to evaluate the biological activity of the secreted antibody. A sandwich-type ELISA was performed. Polysorp plates were coated with NeuGcGM3 ganglioside solution in methanol (10 µg/ml). As secondary antibody an anti-human heavy chain goat antibody coupled to alkaline phosphatase was used. All samples were adjusted to 1 µg/ml antibody concentration and diluted 1/10 in the ELISA test. All tested samples showed recognition of the ganglioside antigen, while clones 31E7 and 35D6 showed values between 70-80% with respect to the positive control (FIG. 8).

Figure 9:
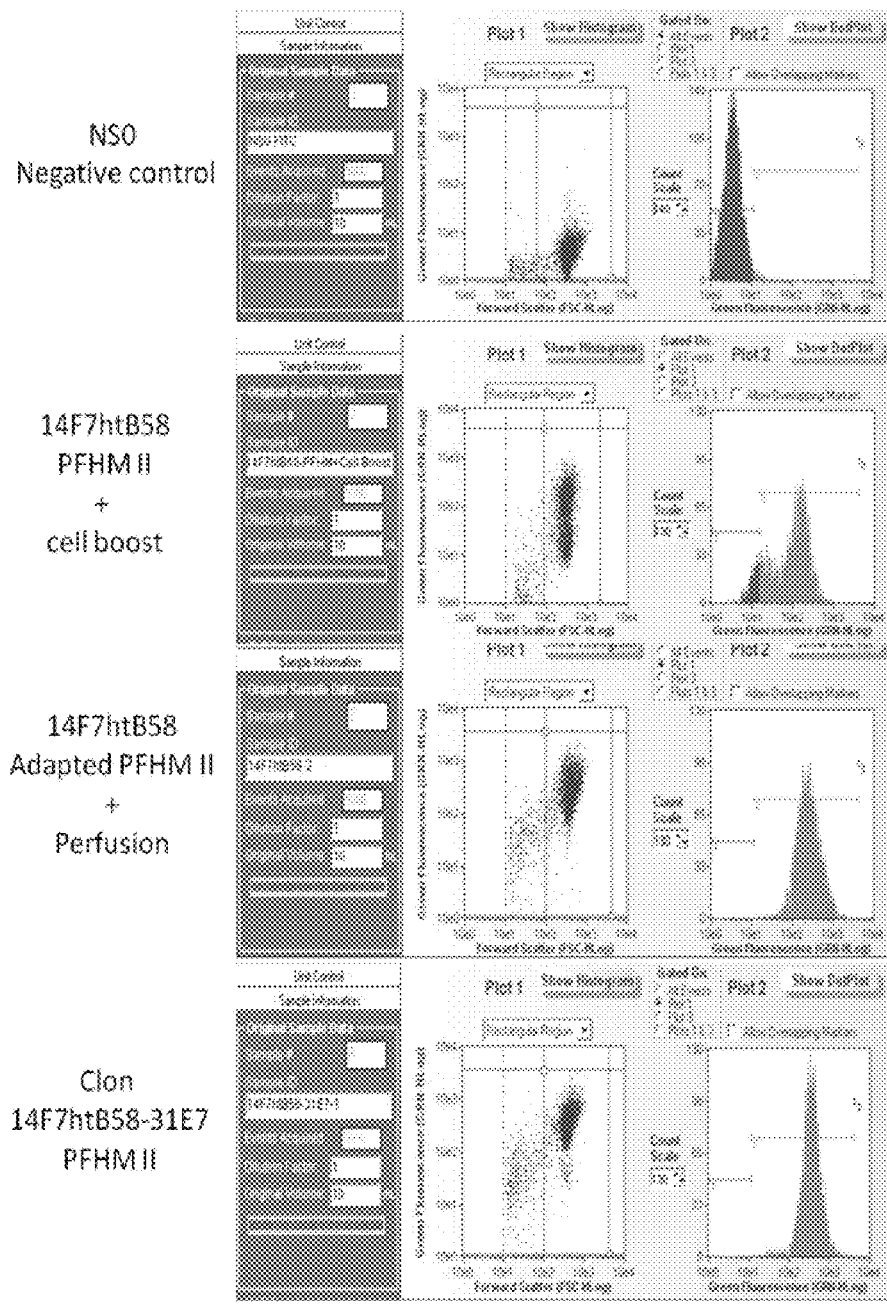
FIG. 9: IgG intracellular concentration measured by flow cytometry at different steps of the selection process.
Figure 10:
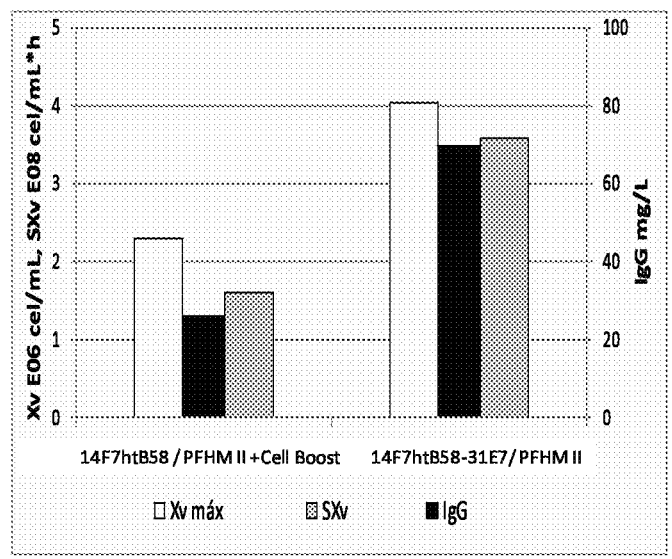
FIG. 10: Comparative kinetic studies between parental cells and clone 31E7 performed in 5 L bioreactor. Xv: viable cell concentration; SXv: integral of viable cells; IgG: maximum antibody concentration.

The intracellular IgG content evolved along the process of phenotypic adaptation and cloning. Parental cells 14F7htB58 growing in PFHMII plus Cell Boost 5 showed a bimodal distribution because of the existence of a non-producer cell sub-population. After adaptation to grow at high densities in PFHMII medium 14F7htB58 cells were enriched in the producer cell sub-population (unimodal distribution), however for clone 31E7 a narrower single peak was obtained suggesting a more homogeneous cell sub-population (FIG. 9). In fact, clone 31E7 has higher maximal cell concentration, integral of viable cells and antibody production rate than parental cells (FIG. 10)

Example 4: Long-Term Stability Studies of High Producer Cell Clones

Figure 11:
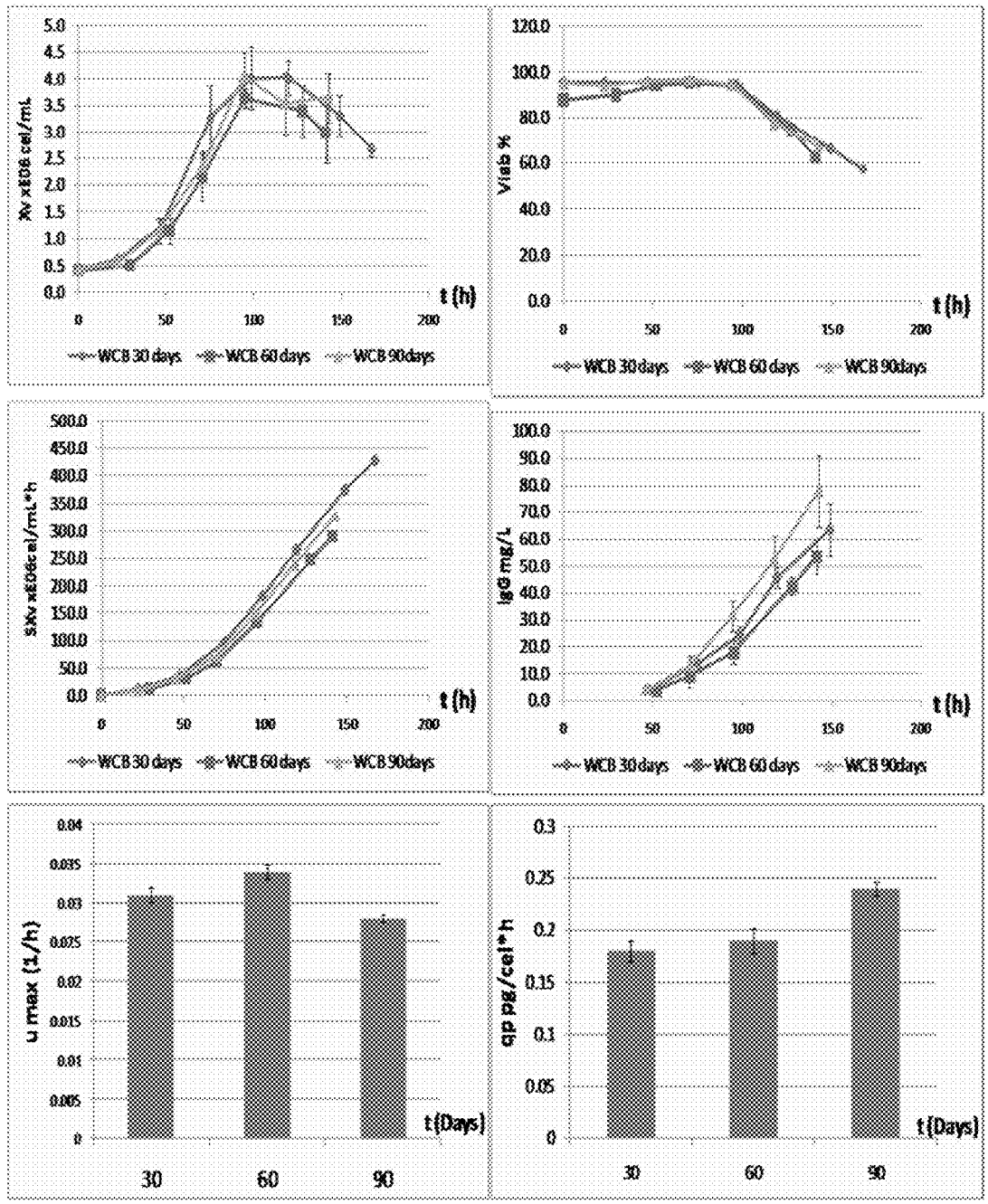
FIG. 11: Kinetic studies to evaluate the stability of clone 31E7 were performed at 30, 60 and 90 days after cell thawing. Cell concentration (Xv), cell viability (%), integral of viable cells (SXv), IgG concentration, maximum growth rate (p) and specific production rate (QP) were measured.
Figure 12:
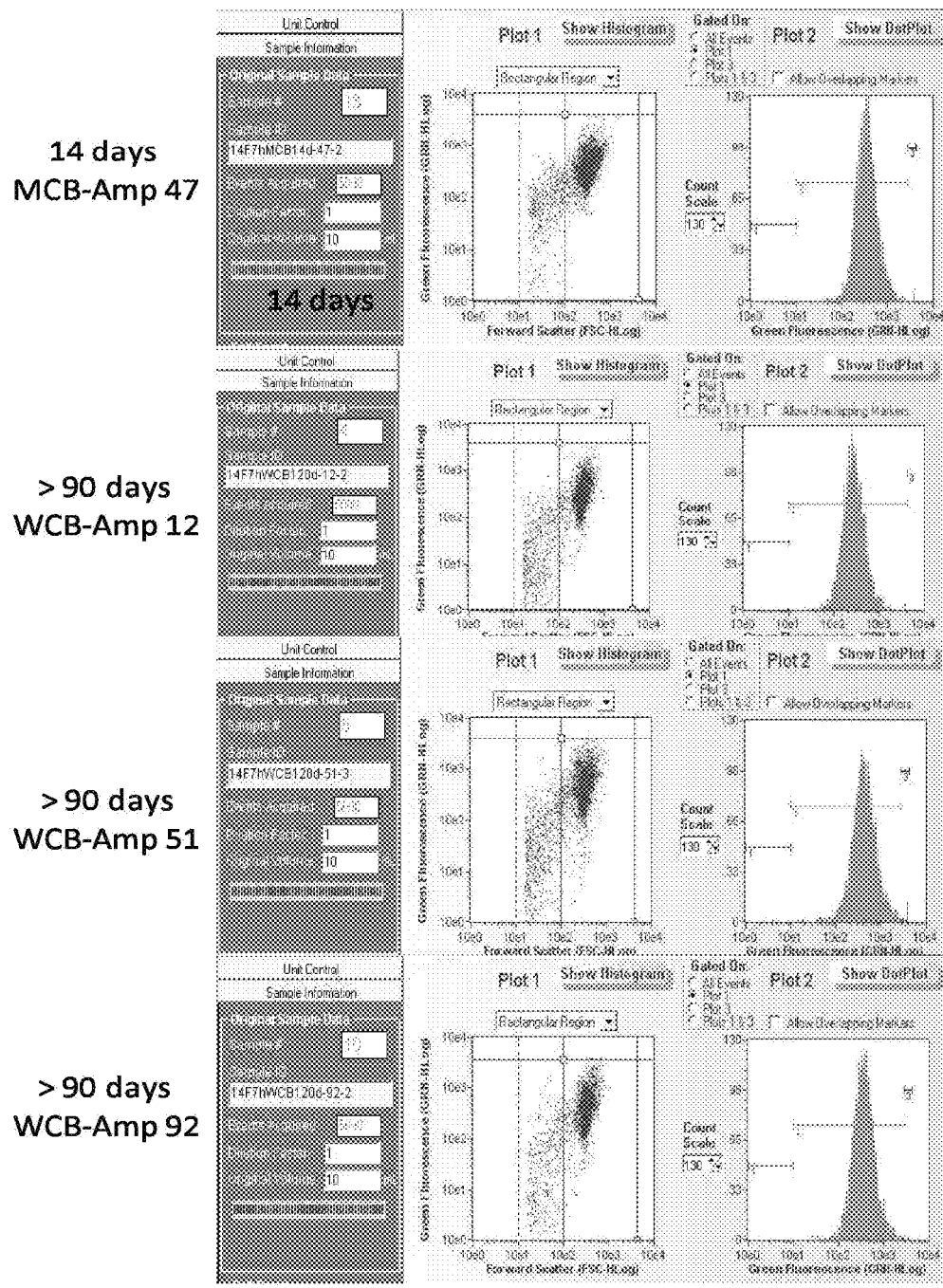
FIG. 12: IgG intracellular content measured by flow cytometry in samples from the stability study of clone 31E7.

The stability of antibody production by clone 31E7 was evaluated during 90 days in cell culture. Kinetic studies in roller bottles were performed at 30, 60 and 90 days after cell thawing. Samples were taken to carry out flow cytometry studies. No differences were found between cells having different times in cell culture. Maximal cell concentration varied from 3.5-4.5×10$^6$ cell/ml, cell viability was higher than 90% and the antibody concentration ranged from 50-80 mg/L (FIG. 10). The growth specific rate (µ) kept higher than 0.025 h$^{-1}$ while the production specific rate (QP) was higher than 0.18 pg/cell*h (FIG. 11). After 90 days in cell culture clone 31E7 showed a narrow single peak at same FMI representative of a homogeneous high producer cell population (FIG. 12).

Example 5: Identity Attributes of the Secreted Immunoglobulin by Selected Stable High Producer Cell Clone 31E7

Figure 13:
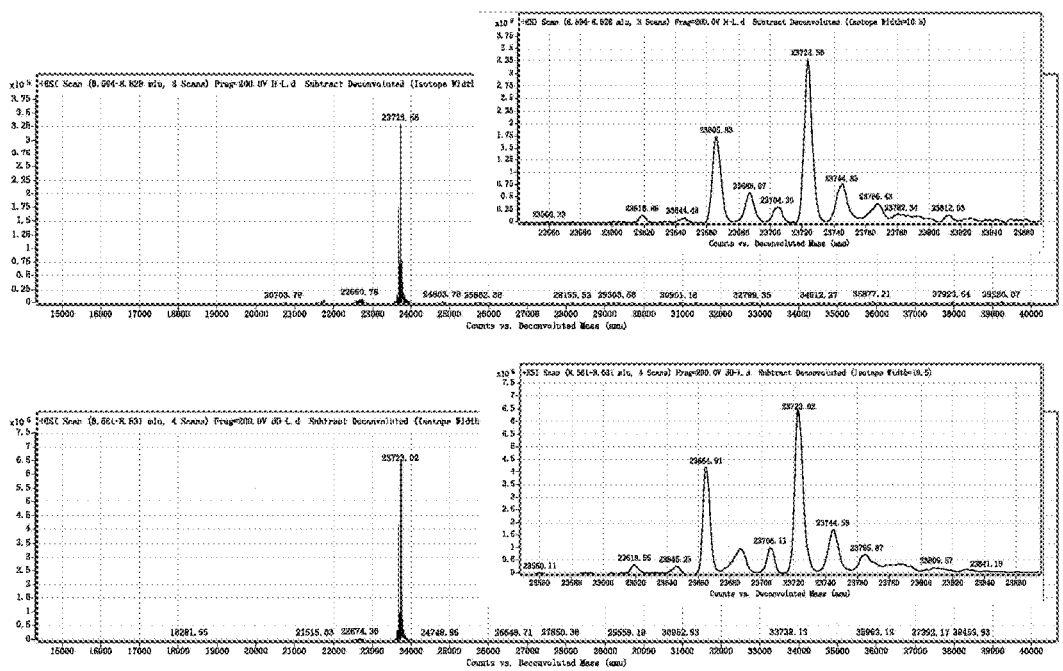
FIG. 13: Deconvoluted mass spectrum of 14F7h Light Chain in its native (upper panel) and deglycosylated (lower panel; using PNGase F) states for the samples being reduced/alkylated. Conventional LC-MS conditions were used with a C8 column for sample separation/desalting and Acetonitrile/Formic acid buffer system for running. Inserted figure corresponds to magnification of main peak region.
Figure 14:
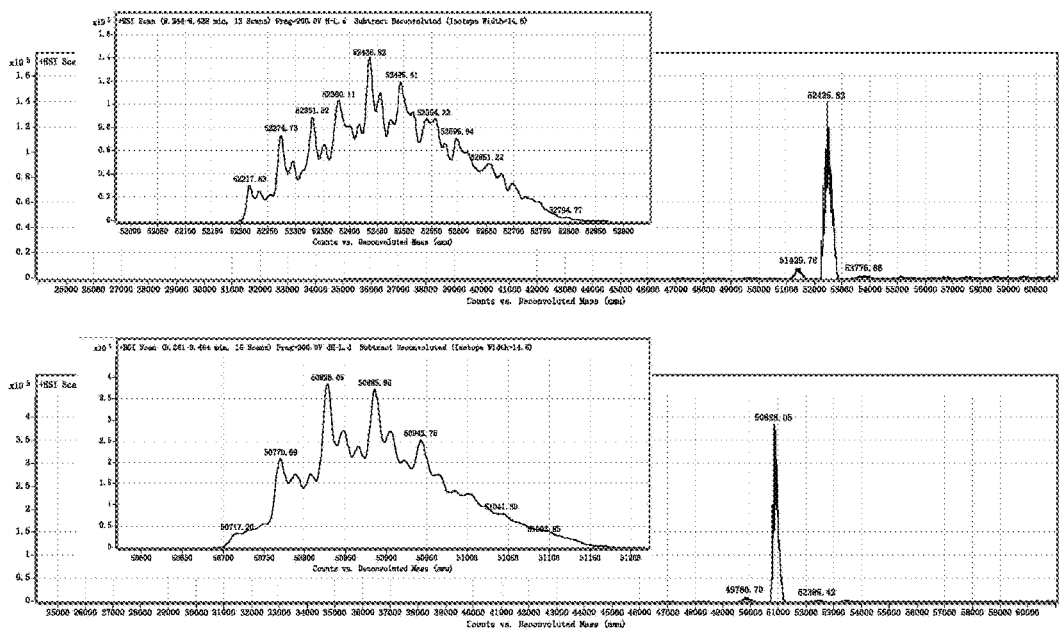
FIG. 14: Deconvoluted mass spectrum of 14F7h Heavy Chain in its native (upper panel) and deglycosylated (lower panel; using PNGase F) states for the samples being reduced/alkylated. Conventional LC-MS conditions were used with a C8 column for sample separation/desalting and Acetonitrile/Formic acid buffer system for running. Inserted figure corresponds to magnification of main peak region.
Figure 15:
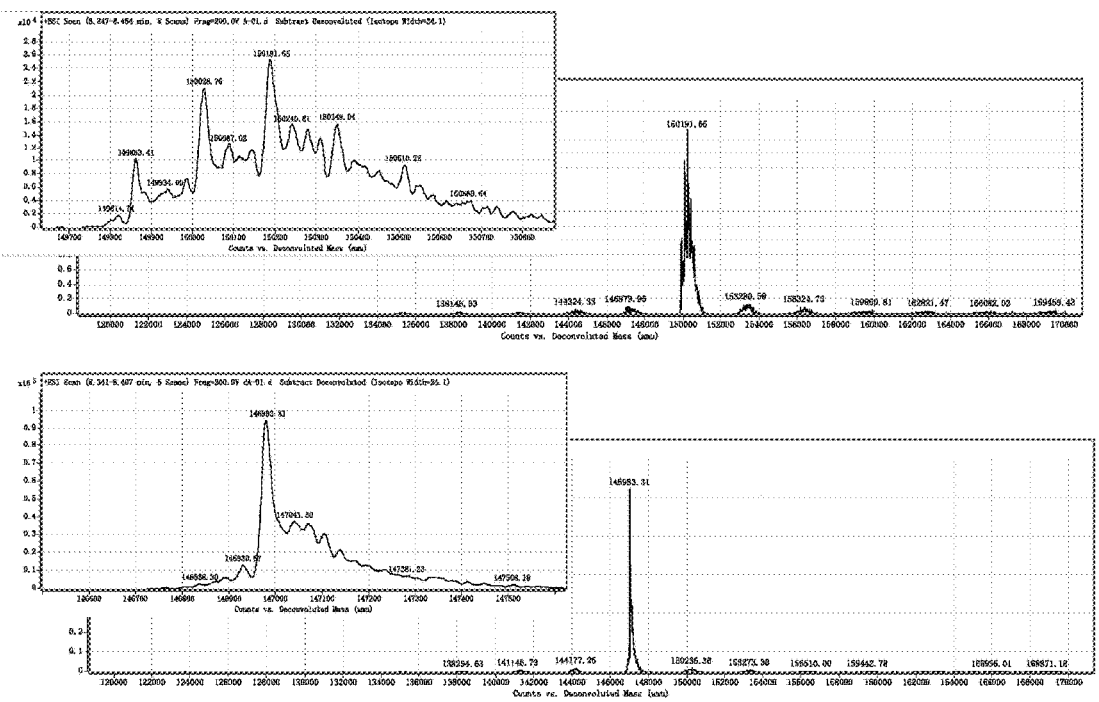
FIG. 15: Deconvoluted mass spectrum of 14F7h Whole Molecule in its native (upper panel) and deglycosylated (lower panel; using PNGase F) states. Conventional LC-MS conditions were used with a C8 column for sample separation/desalting and Acetonitrile/Formic acid buffer system for running. Inserted figure corresponds to magnification of main peak region.
Figure 16:
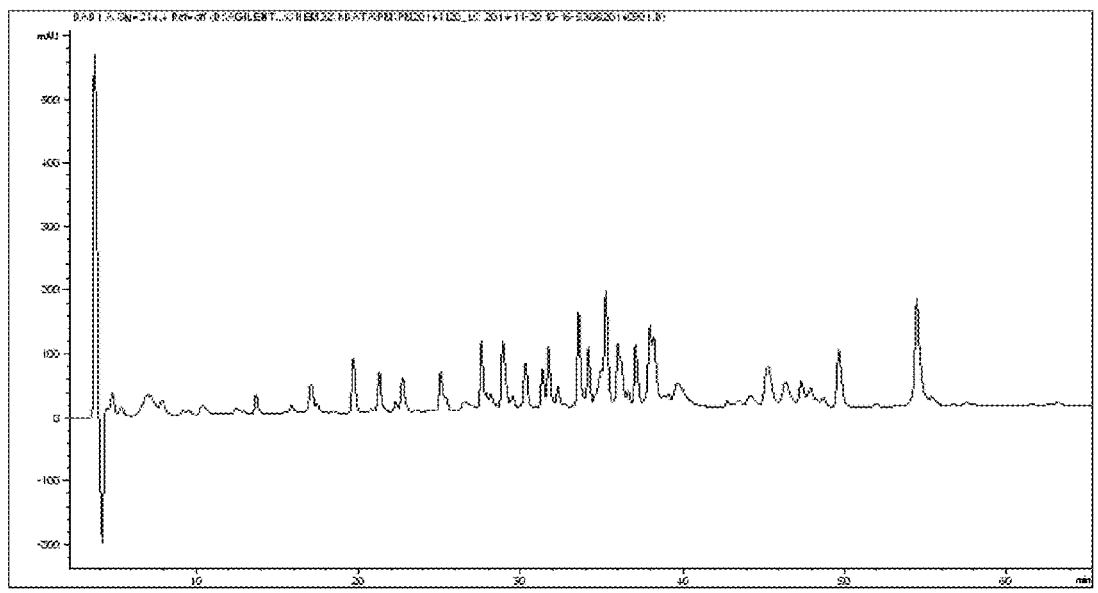
FIG. 16: Peptide mapping profile of 14F7h obtained after trypsin digestion and reverse phase HPLC separation using a C4 column and a conventional Acetonitrile/TFA buffer system.

Several identity attributes are defined to cover the basic molecular properties that later will allow to assess quality of the molecule and to monitor product consistency as well as cell line stability. Primary structure is studied by determination of the mass of the whole molecule, and its individual chains, by LC-ESI-MS analysis of the native and disulfide bridges reduced/alkylated sample (glycosylated and deglycosylated). See Table 1 for a summary of the results and FIGS. 13, 14, 15. Additionally, the peptide mapping of the molecule is used to monitor its first order structure and further exclude any possible post-translational modification truncation or sequence changes (FIG. 16).

TABLE 1

Masses of the complete molecule and its chains with and without glycosylation.

| | Mass (Da) | | | |
|---|---|---|---|---|
| | No | PNGase F | | |
| Species | PNGase F | Observed | Theoretical | % Difference |
| Whole molecule | 149863.41 | 146983.31 | 147009.30[a] | 0.018 |
| Heavy Chain | 52217.63 | 50770.69[b] | 50784.12[c] | 0.026 |
| Light Chain | 23665.93 | 23664.91[b] | 23664.25[d] | −0.0028 |

Figure 17:
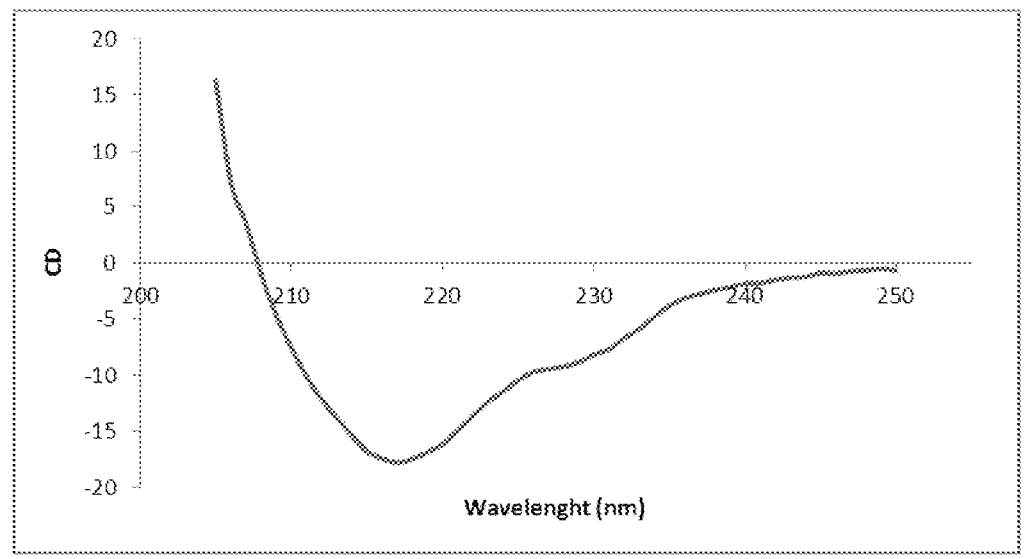
FIG. 17: Circular Dichroism spectral analysis of 14F7 in the Far UV (205-260 nm) region obtained at 25° C. using a 2 mm path length cuvette. The spectra was obtained with a sample concentration of 0.6 mg/mL.
Figure 18:
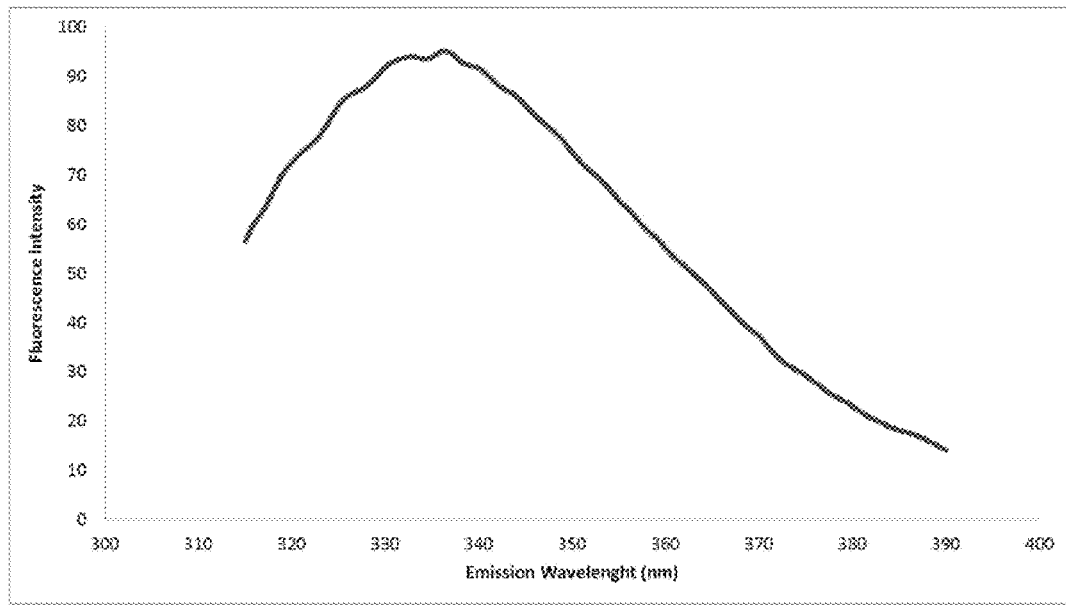
FIG. 18: Fluorescence emission of Tryptophan, using a Varioskan Flash equipment, read between 310 and 390 nm and obtained after exciting 14F7h molecule at 280 nm. A 96 well plate format was used, with 200 uL per well and a sample concentration of 0.2 mg/mL.

[a]Considering lack of K in the C-terminal region of both heavy chains
[b]Reduced with Dithiothreitol and alkylated with Iodoacetic acid
[c]Considering lack of K in the C-terminal region and Iodoacetic acid modification
[d]Considering Iodoacetic acid modification Higher order structures are tested at two levels by using Far UV CD spectra for the analysis of secondary structures (yielding the profile shown in FIG. 17) and Intrinsic Fluorescence properties that allows to detect differences in conformation and protein stability (Weichel et al, 2008, BioProcess International, June). FIG. 18 shows the results obtained for this latter test. In this case, emission maximum was obtained at 333 nm and the value of Absorbance $Ratio_{330\ nm/350\ nm}$ was 1.23.

Figure 19:
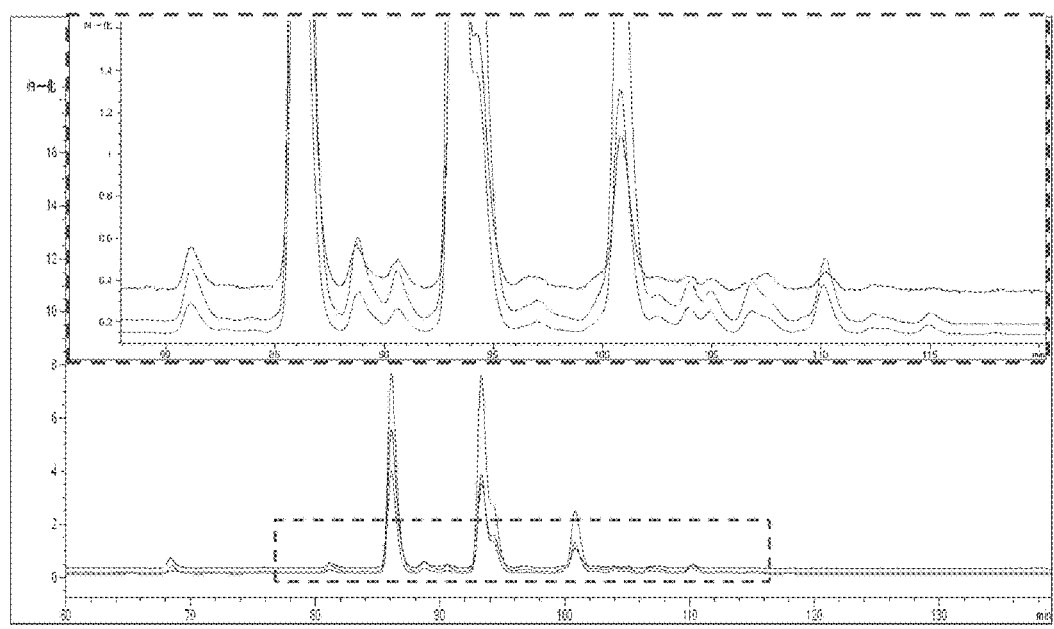
FIG. 19: Glycosylation profiling of 2-AB labeled glycans isolated from 14F7h and separated using normal phase HPLC with fluorescent detection (Ex: 330 nm/Em: 420 nm). Squared broken lines show a magnification of the minor peaks.
Figure 20:
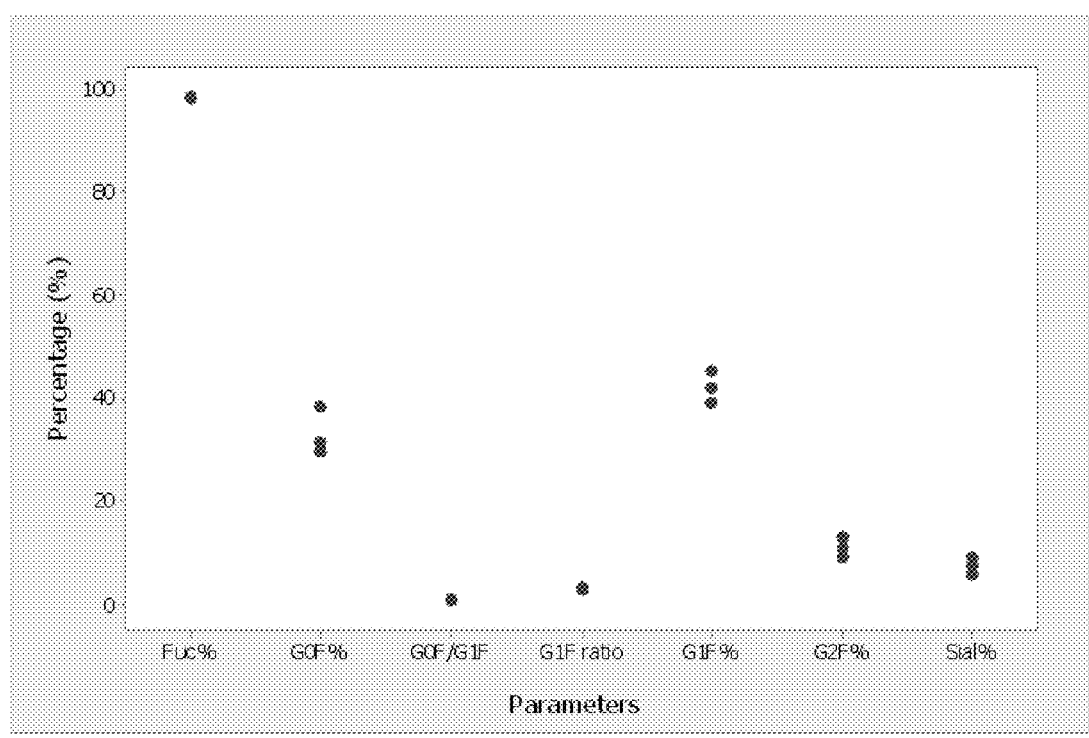
FIG. 20: Glycosylation parameters from different samples (N=3) of 14F7h used to study ranges of variation for glycosylation profiling.

Glycosylation, being the major post-translational modification occurring in human IgG1 antibody molecules, is studied by normal phase HPLC profiling. FIG. 19 shows the results obtained for three different samples, and their glycosylation parameters are shown in Table 2 (Montesino et al, 2012, Biologicals 40:288-298). The behavior and dispersion of these glycosylation parameters are shown in FIG. 20.

TABLE 2

Glycosylation parameters from different samples (N = 3) of 14F7h used to study ranges of variation for glycosylation profiling.

| Samples | G0F % | G1F % | G2F % | G0F/G1F | G1F ratio | Fuc % | Sial % |
|---|---|---|---|---|---|---|---|
| 1 | 31.31 | 41.83 | 10.78 | 0.75 | 3.28 | 98.15 | 8.81 |
| 2 | 29.52 | 45.15 | 13.04 | 0.65 | 3.18 | 98.50 | 7.41 |
| 3 | 38.47 | 39.05 | 8.99 | 0.99 | 2.67 | 98.53 | 5.50 |
| Average | 33.1 ± 11.7 | 42.0 ± 7.5 | 10.9 ± 5.1 | 0.8 ± 0.3 | 3.0 ± 0.9 | 98.4 ± 0.6 | 7.2 ± 4.2 |

Figure 21:
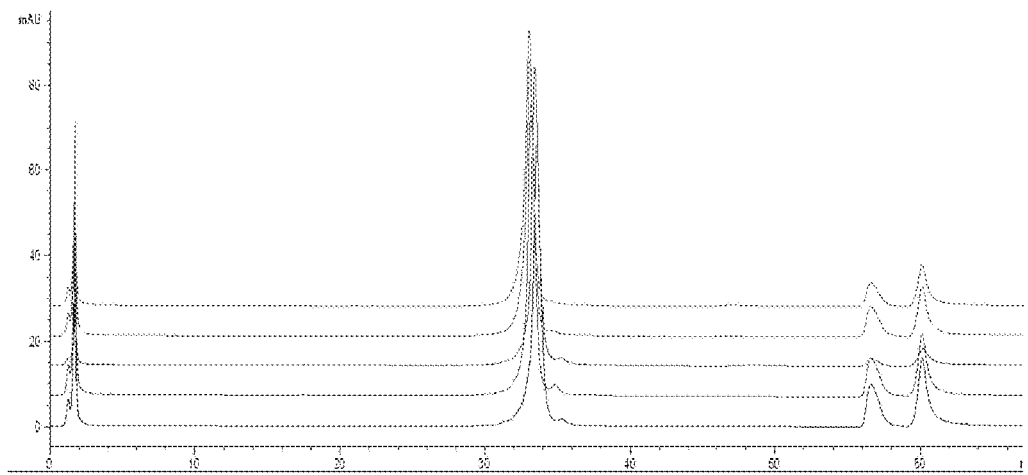
FIG. 21: Weak cation exchange profile of 14F7h using a Propac-WCX10 column, obtained at 280 nm. 30 ug of sample were injected.
Figure 22:
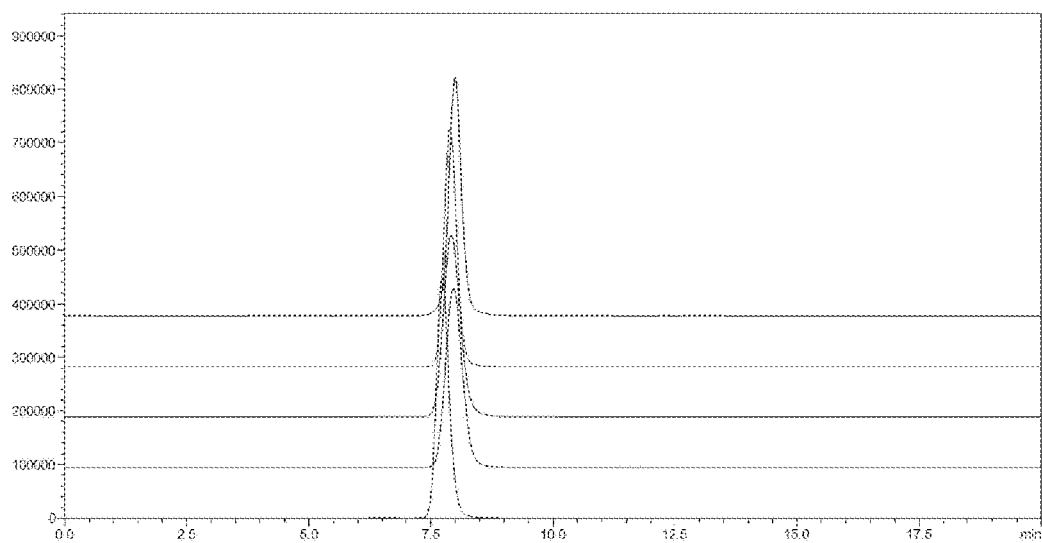
FIG. 22: SEC-HPLC profile of 14F7 using a TSK-G3000sxl column, obtained at 280 nm.

G0F %, G1F %, G2F %: % of agalactose, monogalactose and digalactosylated fucosylated glycans,
Fuc %: % of Fucosylated glycans,
Sial %: % of Sialylated glycans The heterogeneity of the molecule is defined by two orthogonal methods. In the first place Weak Cation Exchange (WCX) is used to detect the different charged species, allowing detecting product truncations, deamidations, some glycosylation variants, etc. For antibodies, results of this method mainly monitor C-terminal lysine truncation, a common modification found in hIgG1 molecules (Dionex Application Note 127, http://www.dionex-france.com/library/literature/application_notes_updates/AN127_LPN1047.pdf). The profiles obtained for different samples are shown in FIG. 21 and Table 3 shows the result of their integration. Additionally, Size Exclusion Chromatography (SEC) is used to monitor the aggregation state of the molecule. FIG. 22 shows the profiles obtained from different samples and Table 4 shows the result of their analyses.

TABLE 3

WCX-HPLC integration results (main peak percentage) for different 14F7h samples.

| Samples | Main Peak % |
|---|---|
| 1 | 96.2 |
| 2 | 95.0 |
| 3 | 95.7 |
| 4 | 96.5 |
| 5 | 96.6 |
| Average | 96.0 ± 1.8 |

TABLE 4

SEC-HPLC integration results (main peak percentage) for different 14F7h samples.

| Samples | SE-HPLC Main Peak % |
|---|---|
| 1 | 99.9 |
| 2 | 99.9 |
| 3 | 99.9 |
| 4 | 99.8 |
| 5 | 99.7 |
| Average | 99.8 ± 0.3 |

Figure 23:
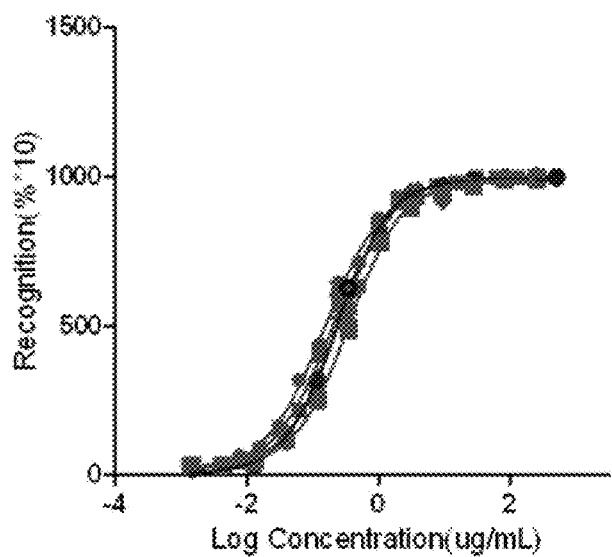
FIG. 23: Flow cytometer dose-response curve (% positive vs log of 14F7h concentration (ug/mL)) using L1210 target cells for different samples of antibody tested on different days.

Finally, the function of the molecule is primarily assessed by studying its ability to recognize its antigen on target cells measured by Flow Cytometry. FIG. 23 shows the dose-response curve results obtained using different samples, and Table 5 shows the $EC_{50}$ calculated from them.

TABLE 5

$EC_{50}$ results for different tests of flow cytometer dose-response curve (% positive vs log of 14F7h concentration (ug/mL)) using L1210 target cells for different samples of antibody tested on different days.

| Test | Sample | $EC_{50}$ (µg/mL) |
|---|---|---|
| 1 | 1 | 0.1633 |
| | 2 | 0.2121 |
| 2 | 1 | 0.2524 |
| 3 | 2 | 0.2409 |
| 4 | 2 | 0.3554 |
| Average | | 0.245 ± 0.180 |

Example 6: Evaluation of the In Vitro and In Vivo Anti-Tumor Effect

Figure 24:
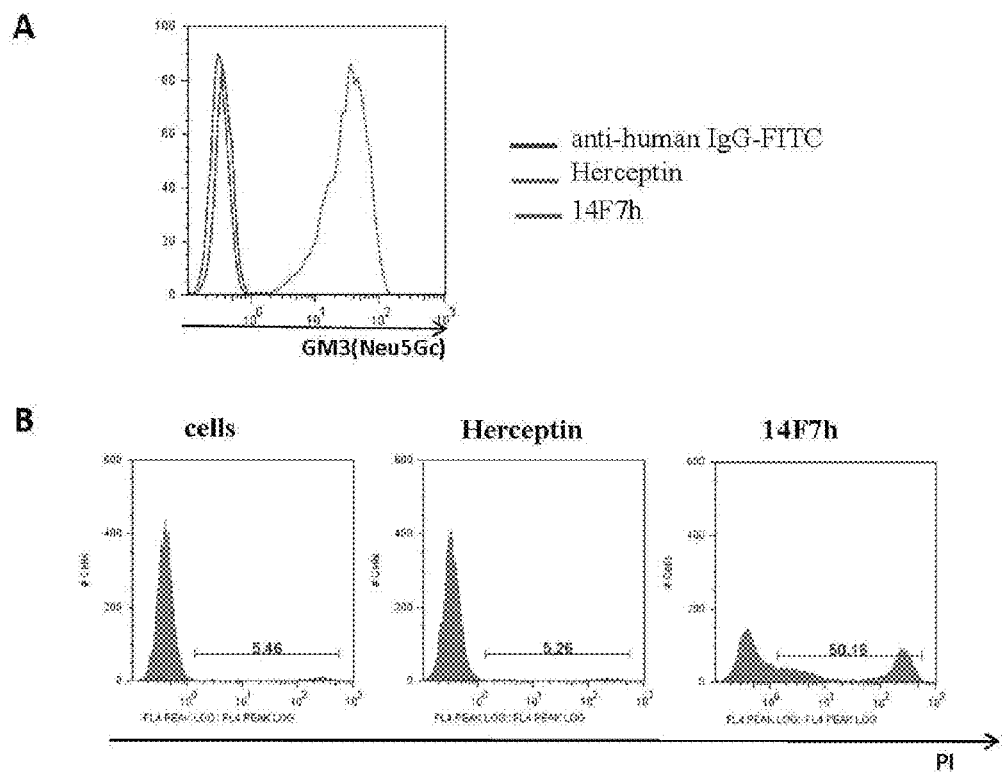
FIG. 24: Cytotoxic effect induced by 14F7h mAb in X63 mouse myeloma cells. (A) Binding properties of 14F7h mAb. X63 cells were stained with 10 μg/mL of the antibody followed by a FITC-conjugated rabbit anti-human IgG antibody. Herceptin mAb (anti-human Her-2) was used as negative control. (B) X63 cells were treated with 100 μg/mL of 14F7h mAb. Cell viability after 6 h incubation at 37° C. was evaluated by propidium iodide (PI) uptake and flow cytometry analysis. Cytotoxicity is expressed as percentage of PI-stained cells. Herceptin mAb was used as negative control.

Antigen expression by X63 mouse myeloma cells was measured by flow cytometry. 100% of X63 mouse myeloma cells were stained by 14F7h mAb (FIG. 24A). X63 cells were incubated with 10 µg/mL of the antibody followed by a FITC-conjugated rabbit anti-human IgG antibody. Herceptin mAb (anti-human Her-2) was used as negative control.

In vitro cytotoxic effect induced by 14F7h mAb in X63 mouse myeloma cells was assessed. X63 cells were treated with 100 µg/mL of 14F7h mAb. Cell viability after 6 h incubation at 37° C. was evaluated by propidium iodide (PI) uptake and flow cytometry analysis. Cytotoxicity is expressed as percentage of PI-stained cells. More than 50% of tumor cells were dead after treatment (FIG. 24B). Herceptin mAb was used as negative control.

Figure 25:
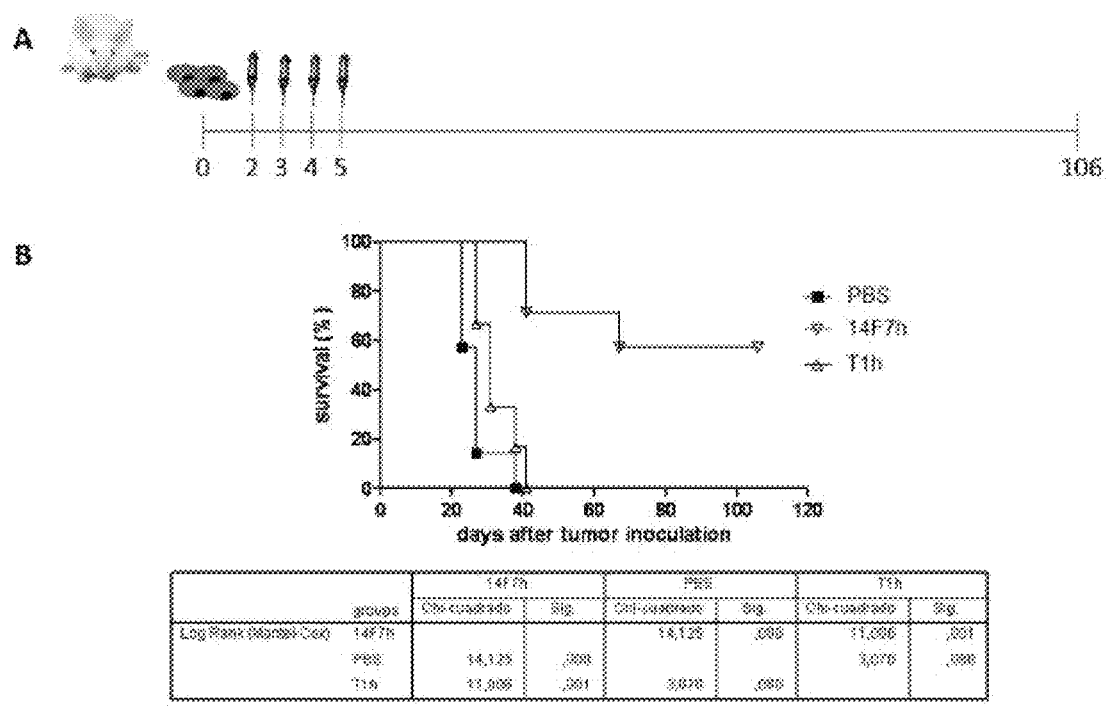
FIG. 25: In vivo anti-tumor effect of 14F7h mAb on a mouse myeloma model. (A) Schedule of mAb administration. X63 mouse myeloma cells ($0.2 \times 10^6$) were inoculated subcutaneously at day 0 to BALB/c mice and the antibodies were administered intravenously (300 μg) at days 2 to 5. (B) Kaplan-Meier curves of tumor-free survival up to day 106. Humanized T1h mAb (anti-human CD6) was used as negative control. Statistical analysis was performed with the log-rank test.

To assess the in vivo anti-tumor effect of 14F7h mAb on X63 mouse myeloma model, $0.2 \times 10^6$ X63 tumor cells were inoculated subcutaneously at day 0 to BALB/c mice and the antibodies were administered intravenously (300 µg) at days 2 to 5 (FIG. 25A). Kaplan-Meier curves of tumor-free survival up to day 106 are shown in FIG. 25B. Statistically significant increase in tumor-free survival was obtained 60% of mice treated with 14F7h mAb were still alive after the follow up time. Humanized T1h mAb (anti-human CD6) was used as negative control. Statistical analysis was performed with the log-rank test.

The invention claimed is:

1. A method for obtaining stable producer cell clones from myeloma cell lines in protein-free medium producing recombinant antibodies for industrial purposes that comprise three stages:
   I. placing the myeloma cell lines into a protein-free, lipid-enriched-supplement medium and performing a stepwise reduction of the lipid-enriched supplement until the lipid-enriched supplement is removed, wherein the stepwise reduction comprises the lipid-enriched-supplement first being in a concentration of about +3.5 g/L until Xv reaches a constant value, then the lipid-enriched-supplement being in a concentration of about +1 g/L until Xv reaches a constant value,
   II. and then growing the cell lines, wherein the cell density is about $1.5 \; 1.8 \times 10^6$ cells/ml, thereby producing myeloma cell lines adapted to protein-free medium,
   III. placing the myeloma cell lines adapted to protein-free medium into a perfusion fermentation system, wherein the cell density is about $5\text{-}10 \times 10^6$ cells/ml, and
   IV. selecting stable producer cell clones from cell lines at the end of fermentation of stage II.

2. The method of claim 1 wherein in stage I the myeloma cell lines are grown in protein-free medium without any supplement for 60 days.

3. The method of claim 1 wherein stage II comprises the following steps:
   I. keeping the myeloma cell lines adapted to protein-free medium in the perfusion fermentation system in 5 L bioreactor for more than 21 days, wherein the medium is adapted to a cell density of $5\text{-}10 \times 10^6$ cells/ml, and
   II. freezing the myeloma cell lines after fermentation and storing in liquid nitrogen.

4. The method of claim 1 wherein stage III comprises the following steps:
   I. subjecting the myeloma cell lines of Stage II to cell cloning by a limiting dilution method,
   II. detecting Antibody-secreting clones,
   III. quantifying an antibody-producer cell sub-population in selected clones, and
   IV. selecting clones by specific growth and specific production.

5. The method of claim 1 wherein the myeloma cell line is the NS0 cell line containing a sequence encoding for the humanized recombinant antibody anti-NeuGcGM3 14F7h.

* * * * *

UNITED STATES PATENT AND TRADEMARK OFFICE
CERTIFICATE OF CORRECTION

| | | |
|---|---|---|
| PATENT NO. | : 10,457,747 B2 | Page 1 of 1 |
| APPLICATION NO. | : 15/549087 | |
| DATED | : October 29, 2019 | |
| INVENTOR(S) | : Chea et al. | |

It is certified that error appears in the above-identified patent and that said Letters Patent is hereby corrected as shown below:

In the Claims

<u>Claim 3, Column 12, Line 17:</u>
Now reads: "stage H"
Should read: --stage II--

Signed and Sealed this
Seventeenth Day of March, 2020

Andrei Iancu
*Director of the United States Patent and Trademark Office*